United States Patent [19]

Haerle et al.

[11] Patent Number: 5,599,407
[45] Date of Patent: Feb. 4, 1997

[54] METHOD FOR ESTIMATING INCLUSION CONTENT OF METALS USING REFLECTANCE

[75] Inventors: Andrew G. Haerle, Houston; Barry A. Mikucki, Lake Jackson, both of Tex.

[73] Assignee: The Dow Chemical Company, Midland, Mich.

[21] Appl. No.: 536,882

[22] Filed: Sep. 29, 1995

[51] Int. Cl.⁶ .............................. C22C 1/00; C22C 33/00
[52] U.S. Cl. .......................... 148/508; 148/500; 148/505
[58] Field of Search ................................. 148/508, 505, 148/500

[56] References Cited

PUBLICATIONS

Shephard, H. D. et al. The Nature of Inclusions In Tensile Fractures of Forging Steels, Oct. 1948, 148/508.

*Primary Examiner*—Deborah Yee
*Attorney, Agent, or Firm*—Timothy S. Stevens

[57] ABSTRACT

A method for estimating the inclusion content of a metal, the method involving three steps. The first step is to section the metal to create an exposed inner surface of the metal. The second step is to measure the reflectance of the exposed inner surface of the metal. The third step is to estimate the inclusion content of the metal from the reflectance. When a physical property of the metal, such as tensile strength, elongation or impact strength, is related to the inclusion content of the metal, then the physical property can be estimated from the reflectance of the exposed inner surface of the metal.

17 Claims, 2 Drawing Sheets

METHOD FOR ESTIMATING INCLUSION CONTENT OF METALS USING REFLECTANCE

BACKGROUND

This invention relates to a process for estimating the inclusion content of metals. In addition, this invention can be used to estimate any physical property of a metal if the physical property is dependent on its inclusion content.

Metal producers often have the need to quantify inclusion content in metals. Inclusions include materials such as oxides, nitrides, sulfides, and other foreign matter which is present in the metal. For example, magnesium oxide is a common inclusion found in magnesium and magnesium alloys. Inclusion content is important because inclusions can lead to diminished physical properties of the metal, propagation of cracks, and ultimate failure of the metal.

The common methods for determining inclusion content are lengthy, time consuming and expensive. A typical method for determining inclusion content involves light microscopy on a polished and etched metal surface, also known as light optical metallography. Optical metallography requires multiple steps: sectioning, grinding, polishing, etching, and examination. Sectioning exposes an inner surface of the metal. Grinding flattens the exposed surface. Polishing makes the exposed surface scratch-free and is accomplished using electrolytic, chemical, or mechanical methods. Etching is accomplished using electrolytic or chemical methods in order to better reveal the microstructure of the sample. Examination typically occurs under a microscope, where the inclusions are counted and analyzed. An image analyzer can be used to count the inclusions. Inclusion content may be expressed as weight percent, volume percent, area percent, number per unit area or any other similar quantity.

The above technique is relatively expensive and is sometimes difficult to employ since the number of inclusions per unit area of a polished surface may be relatively small. On the other hand, a fracture often propagates along a path of inclusions. Thus, there are generally more inclusions visible on a fractured surface than on a flat polished surface. As a result, fractography, the study of fractured surfaces of metals, is another method of inclusion analysis. In fractography, a sample of metal is fractured, and the fractured surface is examined for inclusions. Inclusion content is usually expressed as the number of inclusions per unit area of fracture surface. Accurate fractographic examination occurs under a light optical microscope. Fractographic examination using a microscope is relatively expensive, slow and cumbersome.

Light optical metallography of polished metal surfaces and fractography are difficult to utilize in clean die casting metals where the inclusion content is relatively low. As a result, inclusion concentrating techniques are often used to facilitate analysis of such metals. Most commonly, molten metal is pulled through a porous ceramic filter, forming a cake of inclusions next to the filter, and the metal and filter cake are frozen with the ceramic filter contained therein. The filter cake of inclusions is then analyzed using light optical metallography as described above. Again, this technique is expensive, slow, and cumbersome.

Another method of measuring the inclusion content of metals that has gained some acceptance in the aluminum industry is the use of a Liquid Metal Cleanliness Analyzer (LMCA). In order to use a LMCA, a tube with a small non-conducting orifice is immersed in molten metal. As the molten metal flows through the small orifice, the LMCA electrically counts and sizes the non-metallic inclusions. However, the materials of construction are not suitable for some metals such as magnesium. In addition, the small orifice may become plugged if the metal contains relatively large inclusions. Furthermore, although this method is relatively fast, the measurement instrument is expensive.

Other less common methods for measuring the inclusion content of metals include selective dissolution techniques, neutron activation analysis, glow discharge mass spectrometry, arc-spark emissions spectrometry, distillation, and ultrasonic techniques. However, these methods are also relatively expensive and cumbersome.

Optical metallography, fractography and LMCA are thorough and precise processes. In addition to revealing the inclusion content of a metal, these methods reveal the sizes and shapes of the inclusions. However, metal manufacturers and recyclers are often interested in the inclusion content alone and are not concerned with the size or shape of the inclusions. The thoroughness of optical metallography, fractography, and LMCA is not necessary if inclusion content alone is desired.

Furthermore, as discussed above, these other methods of inclusion analysis are expensive and usually cumbersome procedures. It would be a further advance in the art of inclusion analysis to have a faster, simplified and less expensive instrumental method for determining inclusion content in metals.

SUMMARY OF THE INVENTION

The present invention is a solution to a large degree of the above mentioned problems. Although the instant invention does not measure sizes and shapes of the inclusions as do the traditional methods, the instant invention provides a faster, simplified and less expensive instrumental method for estimating the inclusion content in metals.

The instant invention is a method for estimating the inclusion content in a metal, the method comprising three steps. The first step is to section the metal to create an exposed inner surface of the metal. The second step is to measure the reflectance of the exposed inner surface of the metal. The third step is to estimate the inclusion content of the metal using the reflectance measurement. The preferred means of exposing an inner surface of the metal is to fracture the metal. Any physical property of a metal dependent on its inclusion content can also be estimated using the reflectance measurement.

DETAILED DESCRIPTION OF THE INVENTION

Figure 1:
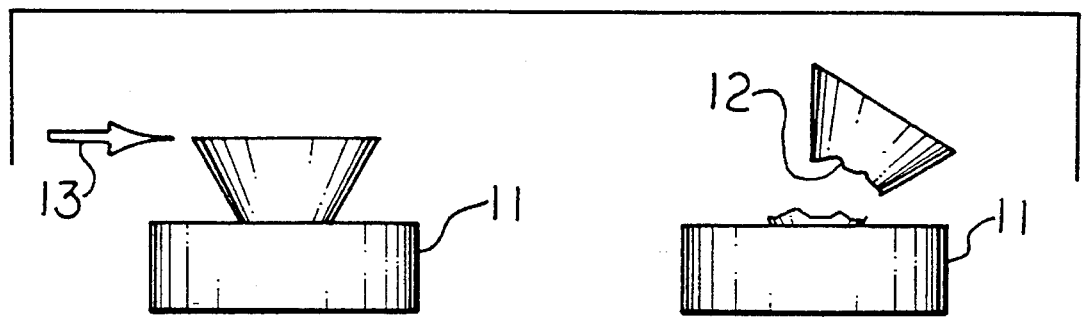
FIG. 1 is an illustration of the surface preparation step according to an embodiment of the instant invention.

Referring now to FIG. 1, therein is shown the first step of an embodiment of the instant invention, which step comprises, as a means of sectioning a metal to expose an inner surface of the metal, fracturing a test casting 11 to create a fractured surface 12. The test casting 11 may be prepared by casting molten metal into a permanent mold. The mold may be any convenient shape, but a test casting 11 such as that in FIG. 1 can be prepared using a disk shaped mold with a cone shaped riser. When force 13 is applied to the test casting 11, such as by a hammer, the test casting 11 breaks and the fractured surface 12 results.

Figure 2:
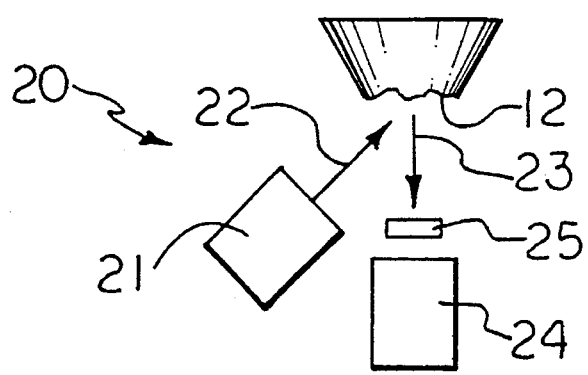
FIG. 2 is an illustration of the measurement of the reflectance of a fractured surface according to an embodiment of the instant invention.

Referring now to FIG. 2, therein is shown the second step 20 of an embodiment of the instant invention. A light source 21 is used to direct incident light 22 onto the fractured surface 12. Some of the incident light 22 is reflected off the fractured surface 12 as reflected light 23 and the resulting reflectance is directed through a 455 nanometer effective wavelength light filter 25 and then measured by a light detector 24.

Reflectance is defined conventionally and herein as the ratio of the intensity of the reflected light from the sample to the intensity of the incident light. The detector 24 in FIG. 2 measures the reflectance at an angle of zero degrees from the perpendicular of the fractured surface 12. However, reflectance at other angles can be measured and integration techniques can be used to measure reflectance at multiple angles of reflectance.

The incident light 22 is directed onto the fractured surface 12 at an angle of forty-five degrees. However, illumination at other angles can be used and integration techniques can be used for illuminating the fractured surface at multiple angles of illumination.

The color, or wavelength, of the incident light 22 is not critical. The incident light 22 may be white light or any other desired color. In FIG. 2, the incident light 22 is white light while the detector 24 measures blue light because of the effective wavelength of the filter 25.

The light source 21 and detector 24 are preferably an optical reflectometer that directly measures reflectance of a surface. For example, one of the following instruments produced by Technidyne Corporation (Albany, Ind.) can be used: the Model S4-M Brightimeter; the Brightimeter Micro S-5; the Technibrite Model TB-1; the Technibrite Micro TB-1C; the Hany-Brite™ Hand-Held Brightness Tester; and the Technidyne Color Touch Spectrometer.

In the embodiment illustrated in FIG. 2, the filter 25 is placed before the detector 24 so that only the reflected light 23 having an effective wavelength of 455 nanometers (blue light) is passed to the detector 24. However, the color, or wavelength, of the reflected light is not critical. White light, green light, amber light, or any other desired wavelength of light may be measured by the detector.

A portion of the incident light 22 is not reflected, because that portion is absorbed by characteristics of the fractured surface such as inclusions. Therefore, the reflectance measured by the detector 24 is related to the inclusion content in the metal.

Figure 3:
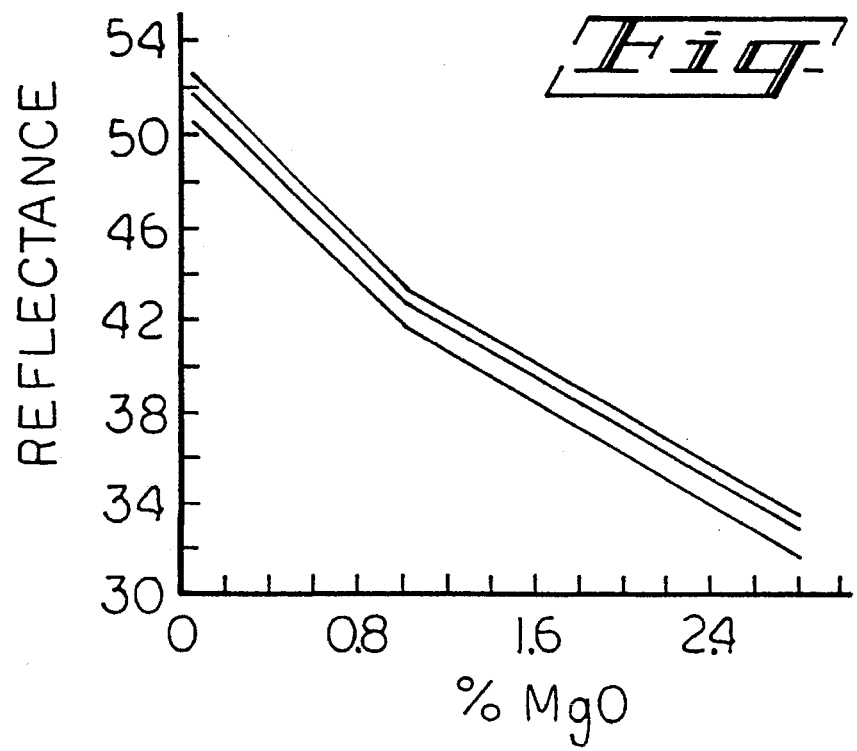
FIG. 3 illustrates the relationship between reflectance and inclusion content for an embodiment of the instant invention using light of different wavelengths.

Referring now to FIG. 3, therein is shown a graph representing the relationship between inclusion content as weight percent magnesium oxide in a magnesium alloy and reflectance of a fractured surface in one embodiment of the instant invention. The top curve in FIG. 3 is obtained using a filter 25 having an effective wavelength of 595 nanometers, i.e., amber light. The middle curve in FIG. 3 is obtained using a filter 25 having an effective wavelength of 557 nanometers, i.e., green light. The bottom curve in FIG. 3 is obtained using a filter 25 having an effective wavelength of 455 nanometers, i.e., blue light.

It should be understood that although the wavelength of illumination and detection are not critical in the instant invention, there may be specific systems where one wavelength will work better than another because of the color of the metal and its inclusions. A few experiments at different wavelengths will indicate which wavelength is better.

A part made from a metal can be sectioned and analyzed as well as a test casting 11. For example, a die-cast rear view mirror mount can be sectioned and analyzed.

In FIG. 3, as the inclusion content increases, the reflectance decreases. Such a graph is a calibration curve that can be used as the third step of the instant invention. In other words, the relationship represented by the graph can equivalently be described by the equation: $i=rk$, where $i$ is inclusion content, $r$ is reflectance and $k$ is a constant. The constant $k$ is a proportionality constant which can be determined if the inclusion content $i$ and the reflectance $r$ are known. The inclusion content used to calibrate this invention can be determined by any of the standard methods such as by microscopic examination of a fractured surface of the metal in question. It should be understood that the value of $k$ may be different for different values of $i$ or $r$ as discussed in greater detail below.

In the particular embodiment of FIG. 3, the metal is a magnesium alloy and the inclusions are magnesium oxide. Magnesium alloy by definition herein is any alloy which contains more than fifty percent magnesium. Likewise an alloy of any other metal is defined herein as any alloy which contains more than fifty percent of such metal.

The graph of FIG. 3 is generated by preparing samples of magnesium alloy under different conditions to vary the inclusion content. Table I lists seven conditions under which the samples are prepared. The samples are then analyzed to determine the weight percent magnesium oxide (MgO) in the magnesium metal. For example, for magnesium alloys, the percent MgO is determined by Neutron Activation Analysis or Glow Discharge Mass Spectroscopy. This analysis gives the value for $i$, which is the x axis in FIG. 3. Table I lists the values for $i$ as MgO (%).

TABLE I

| Sample | How Made | MgO (%) | Reflectance 455 nm | Std. Dev. | 595 nm | 557 nm | Microscopy NMI/in$^2$ |
|---|---|---|---|---|---|---|---|
| 1 | Air/SF$_6$ sparged | 2.686 | 29.9 | ±0.59 | 33.1 | 32.8 | 29832 |
| 2 | 100% Scrap | 1.214 | 34.5 | ±1.54 | | | 18384 |
| 3 | 77% Scrap | 1.109 | 37.3 | ±3.03 | | | 25125 |
| 4 | 54% Scrap | 0.932 | 40.3 | ±0.59 | 43.3 | 43.1 | 15030 |
| 5 | 31% Scrap | 0.995 | 41.9 | ±0.60 | | | 11645 |
| 6 | Virgin Ingot | 0.061 | 48.7 | ±0.99 | | | 600 |
| 7 | Flux Refined | 0.032 | 48.7 | ±1.68 | 52.2 | 51.8 | 359 |

The samples of Table I are analyzed for reflectance using an optical reflectometer The reflectance, $r$, is the y axis in FIG. 3. Ten castings are made for each sample, and each casting is tested for reflectance eight times. Therefore, each sample is tested eighty times. Table I lists the averaged results. Table I also lists the standard deviation for the reflectance tests at 455 nanometers.

The reflectance equals r in the third step of the instant invention. Since the values for r and i are known, the value of k can be determined for this system. The value for k is represented by the slope of the curve in FIG. 3. It should be understood that the value of k may vary depending on the particular metal or inclusion present. The size, optical properties and size distribution of the inclusions will also influence the value of k for this invention. Therefore, an independent value for k should be determined for each system. Furthermore, each individual system might have more than one k value. For example, in FIG. 3, two proportionality constants are illustrated. At inclusion contents below 1% magnesium oxide, the value for k differs from the value of k for inclusion contents above 1% magnesium oxide.

A graph such as that shown in FIG. 3 can be established for any metal or any inclusion. After the graph is generated, the graph can be used to quickly estimate the inclusion content of a piece of metal once the reflectance is known. Such a graph can then be used as a calibration curve for routine quality control purposes.

It should be understood that this invention is a simple, inexpensive method for estimating inclusion content. This method is not intended to be as thorough as the traditional, more expensive methods of determining inclusion content. The difference between the two methods may be observed by comparing the reflectance results with the results derived from the more common method of light microscopy, shown in Table I as the number of non metallic inclusions per square inch (NMI/in$^2$).

Figure 4:
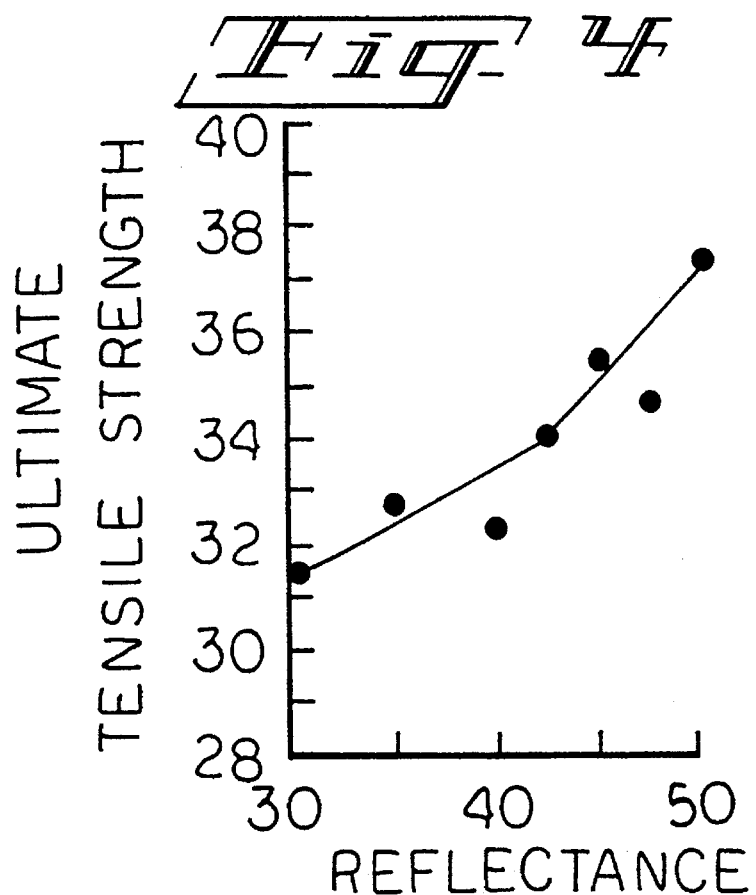
FIG. 4 illustrates the relationship between reflectance and ultimate tensile strength for a magnesium alloy according to an embodiment of the instant invention.
Figure 5:
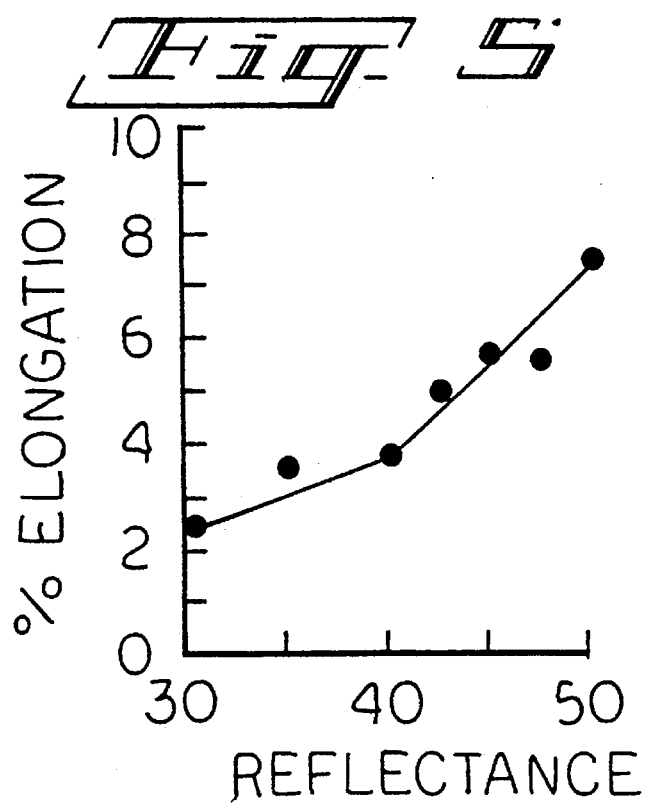
FIG. 5 illustrates the relationship between reflectance and percent elongation for a magnesium alloy according to an embodiment of the instant invention.

Of course, any physical property of a metal which is dependent on the inclusion content of the metal can be similarly estimated. For example, fatigue resistance of a metal can be dependent on the inclusion content of the metal. Similarly, the impact strength of a metal can be dependent on the inclusion content of the metal. In addition, the proportional limit, elastic limit, yield point and every other physical property of a metal can be dependent on the inclusion content of the metal. FIGS. 4 and 5 are related to the dependence of ultimate tensile strength and percent elongation on the reflectance of a fractured metal surface.

Referring now to FIG. 4, therein is shown the relationship between reflectance and ultimate tensile strength for a magnesium alloy whose ultimate tensile strength is a function of its inclusion content. Ultimate tensile strength is an important mechanical property for metals. Inclusions can have a detrimental effect on the ultimate tensile strength. Since the reflectance of a surface is related to the inclusion content for a particular metal, the reflectance may also be related to the ultimate tensile strength of the metal. For the particular embodiment of FIG. 4, as the reflectance increases, the ultimate tensile strength of a test bar increases. Therefore, an increase in MgO inclusion content, which causes a decrease in reflectance, results in a decrease in tensile strength. Therefore, it is equivalent in the instant invention to estimate tensile strength as it is to estimate inclusion content when the tensile strength is a function of the inclusion content.

Referring now to FIG. 5, therein is shown the relationship between reflectance and the percent elongation for a magnesium alloy whose elongation is a function of its inclusion content. Percent elongation is an important mechanical property for metals. Inclusions can have a detrimental effect on the percent elongation. Since the reflectance of a surface is related to the inclusion content for a particular metal, the reflectance may also be related to the percent elongation of the metal. For the particular embodiment of FIG. 5, as the reflectance increases, the percent elongation of a test bar increases. Therefore, an increase in MgO inclusion content, which causes a decrease in reflectance, results in a decrease in elongation. Therefore, it is equivalent in the instant invention to estimate elongation as it is to estimate inclusion content when the elongation is a function of the inclusion content.

Referring now to Table II, therein is shown the relationship between reflectance and the impact strength for a magnesium alloy whose impact strength is a function of its inclusion content. Impact strength is an important mechanical property for metals. Inclusions can have a detrimental effect on the impact strength. Since the reflectance of a surface is related to the inclusion content for a particular metal, the reflectance may also be related to the impact strength of the metal. For the particular embodiment of Table II, as the reflectance increases, the impact strength of a test bar increases. Therefore, an increase in MgO inclusion content, which causes a decrease in reflectance, results in a decrease in impact strength. Therefore, it is equivalent in the instant invention to estimate impact strength as it is to estimate inclusion content when the impact strength is a function of the inclusion content.

TABLE II

| Reflectance | Charpy Impact Strength in Foot-Pounds |
| --- | --- |
| 29.4 | 4.7 |
| 35.1 | 5.2 |
| 45.0 | 4.8 |
| 49.4 | 6.2 |
| 50.8 | 7.0 |
| 52.3 | 7.5 |
| 55.2 | 8.0 |
| 55.7 | 8.2 |
| 56.3 | 8.0 |

What is claimed is:

1. A method for estimating the inclusion content in a metal, the method comprising the steps of:

(a) sectioning the metal to create an exposed inner surface of the metal;

(b) measuring the reflectance, r, of the exposed inner surface of the metal;

(c) estimating the inclusion content, i, of the metal from the relationship $$i = rk$$

where k is a constant.

2. The method of claim 1, wherein the metal is a metal selected from the group consisting of zinc alloys, tin alloys, lead alloys, aluminum alloys, copper alloys, brass, bronze and magnesium alloys.

3. The method of claim 1, wherein the inclusions comprise oxides.

4. The method of claim 2, wherein the inclusions comprise oxides.

5. The method of claim 1, wherein the metal is fractured in step (a) to expose an inner surface of the metal.

6. The method of claim 2, wherein the metal is fractured in step (a) to expose an inner surface of the metal.

7. The method of claim 6, wherein the metal alloy is magnesium alloy and the inclusions comprise magnesium oxide.

8. A method for estimating a physical property of a metal, the physical property being dependent on the inclusion content of the metal, the method comprising the steps of:
  (a) sectioning the metal to create an exposed inner surface of the metal;
  (b) measuring the reflectance, r, of the exposed inner surface of the metal;
  (c) estimating the physical property, p, of the metal from the relationship $$p = rk$$

where k is a constant.

9. The method of claim 8, wherein the metal is a metal selected from the group consisting of zinc alloys, tin alloys, lead alloys, aluminum alloys, copper alloys, brass, bronze and magnesium alloys.

10. The method of claim 8, wherein the inclusions comprise oxides.

11. The method of claim 9, wherein the inclusions comprise oxides.

12. The method of claim 8, wherein the metal is fractured in step (a) to expose an inner surface of the metal.

13. The method of claim 9, wherein the metal is fractured in step (a) to expose an inner surface of the metal.

14. The method of claim 13, wherein the metal alloy is magnesium alloy and the inclusions comprise magnesium oxide.

15. The method of claim 14, wherein the physical property is tensile strength.

16. The method of claim 14, wherein the physical property is elongation.

17. The method of claim 14, wherein the physical property is impact strength.

* * * * *